(12) United States Patent
Jang

(10) Patent No.: US 8,865,659 B2
(45) Date of Patent: Oct. 21, 2014

(54) COMPOSITIONS FOR PREVENTION OR TREATMENT OF HEPATITIS C VIRUS CONTAINING GINSENOSIDE RG3 AS AN ACTIVE INGREDIENT

(71) Applicant: Jae-Young Jang, Seoul (KR)

(72) Inventor: Jae-Young Jang, Seoul (KR)

(*) Notice: Subject to any disclaimer, the term of this patent is extended or adjusted under 35 U.S.C. 154(b) by 0 days.

(21) Appl. No.: 13/690,165

(22) Filed: Nov. 30, 2012

(65) Prior Publication Data

US 2013/0178430 A1 Jul. 11, 2013

(30) Foreign Application Priority Data

Jan. 6, 2012 (KR) .................. 10-2012-0001800

(51) Int. Cl.
| | | |
|---|---|---|
| *A01N 45/00* | (2006.01) | |
| *A61K 31/70* | (2006.01) | |
| *A23L 1/30* | (2006.01) | |
| *A61K 31/704* | (2006.01) | |
| *A61K 47/22* | (2006.01) | |
| *A61K 9/20* | (2006.01) | |
| *A61K 9/00* | (2006.01) | |

(52) U.S. Cl.
CPC .............. *A61K 31/704* (2013.01); *A23L 1/30* (2013.01); *A61K 47/22* (2013.01); *A61K 9/2018* (2013.01); *A61K 9/0019* (2013.01); *A61K 9/2059* (2013.01)
USPC ........................................... 514/24

(58) Field of Classification Search
CPC ................................... A61K 31/704
USPC .......................................... 514/26
See application file for complete search history.

(56) References Cited

U.S. PATENT DOCUMENTS 6,455,078 B1* 9/2002 Wu ............................. 424/725

* cited by examiner

*Primary Examiner* — Traviss C McIntosh, III
(74) *Attorney, Agent, or Firm* — Lexyoume IP Meister, PLLC

(57) ABSTRACT

This invention is for the compound containing ginsenoside Rg3 as an active ingredient to prevent and treat Hepatitis C virus infection. Specifically, the ginsenoside Rg3 of this invention demonstrated the predominant antiviral activities and apotosis actions in a dose-dependent manner in the Hepatitis C virus infected cells (Huh 7.5.1). Confirmed that it reduces the levels of TNF-α and thioredoxin significantly, and increases phospho-NFκB. It also demonstrated same effectiveness as PegInterferone alpha-2b(PegIFN a-2b, Hepatitis C therapeutics), and has no cytotoxicity to human bodies. Thus, it may be used safely as an active ingredient of medical/pharmaceutical and health food compounds for preventing or treating Hepatitis C.

3 Claims, 13 Drawing Sheets

COMPOSITIONS FOR PREVENTION OR TREATMENT OF HEPATITIS C VIRUS CONTAINING GINSENOSIDE RG3 AS AN ACTIVE INGREDIENT

CROSS-REFERENCES TO RELATED APPLICATION

This patent application claims the benefit of higher priority from the Korean Patent Application No. 10-2012-0001800 filed on Jan. 6, 2012, and the contents of which are incorporated herein by reference.

BACKGROUND OF THE INVENTION

1. Field of the Invention

This invention is for a pharmaceutical compound containing ginsenoside Rg3 and/or its pharmaceutically acceptable salts as an active ingredient for preventing and treating Hepatitis C infection

2. Description of the Related Art

Hepatitis C virus (referred as "HCV" hereafter) infection is mainly transmitted via transfusion and community-acquired infection. It is also reported that 70% of kidney dialysis may transmit the HCV infection. It is known that approximately 20% of the infected patients, once infected with HCV, may develop acute hepatitis accompanying liver cirrhosis which may convert to liver cancer in five (5) years (Davis et al, New. Engl. J. Med., 321, 1501, 1989; Alter et al, in Current Pespective in Hepatology, p 83, 1989). This high infection rate of chronic hepatitis is a rare case in RNA infections and it tells that the HCV plays a big role in liver cancer transmission. Since very thorough examinations are conducted for blood samples recently, HCV infection via transfusion is well controlled. However, the HCV infection via community-acquired infection cannot yet be controlled, it appears to be a serious issue world-widely.

According to recent scientific reports, approximately 200 million people are infected with HCV world-widely and 4.5 million people are presumed to be infected with HCV in the USA (it is assumed that the number of 4.5 million could be raised up to 15 million). In Europe, at least 5 million people are presumed to be hepatitis C patients.

Up to now, neither a satisfactory vaccine against Hepatitis C nor an effective therapeutic agent to treat Hepatitis C has yet been available. Therefore, numerous pharmaceutical companies and research institutes all over the world keep trying to invent an effective Hepatitis C treating agent. Compared with Hepatitis B, HCV patients are evenly distributed across the world and demonstrate much higher rate to convert to liver cirrhosis and then to liver cancer. In addition, Hepatitis C also demonstrates a higher rate to convert to chronic hepatitis, and so studies to identify the mechanism for converting to chronic hepatitis are still going on. Hepatitis C virus can be transmitted not only by transfusion but also by intravenous drug injection and by printing tattoos. However, its major transmission is made by direct blood contacts. Once infected with HCV, most of the infected patients may progress to chronic hepatitis and then further to liver cirrhosis and liver cancer. Therefore, it is urgently requested to develop an effective vaccine and a therapeutic agent to treat Hepatitis C. There are many different genotypes available and mutations occur among HCV strains, and so HCV re-infection or co-infection may occurs concurrently once chronic hepatitis is developed by HCV. This is why an effective vaccine invention against HCV is difficult.

The current Hepatitis C treatment is conducted using a combination therapy with Interferon-α with Ribavirin. However, this treatment demonstrates very low rate of cure and brings severe side effects. About 25% of Hepatitis C patients do not respond to Interferon-α and another 25% of patients are apt to setback to the disease after responding temporarily to the medicine. The rest 50% of patients maintain normal ALT level and remain HCV RNA negative even after the treatment finished. Furthermore, those 50% of treated patients relapse into it in 3-6 months from the first treatment. In this case, only 25% of Hepatitis C patients show sustained viral response (SVR) and its treatment effect retains at most six months in those patients. Furthermore, among the six different Hepatitis C virus genotypes, the most common genotype 1b does not respond to Interferon-α so well compared to genotype 2 or genotype 3. In case of combination therapy with Interferon-α and Ribavirin is administered, the treatment is made with double effect. When Ribavirin alone is treated, the treatment effect is not so good and rather brings side effects such as anemia resulted from erythroclasis. So, Ribavirin is prescribed only when a patient does not respond to Interferon-α or Hepatitis C is relapsed. So far, an effective antiviral agent that is specifically targeted to hepatitis C virus with no setbacks/relapsing has not yet been developed.

RNA genome was first isolated from HCV through a molecular cloning in 1989 (Choo, Q-L, et al., 1989, Isolation of a cDNA clone was derived from a blood-borne non-A, non-B viral hepatitis genome. Science 244:359-362). Since then, molecular biological approaches to HCV have been made. However the approaches were limited due to lacks of both efficient cell culture system and animal model. But recently, a hepatoma cell line replicating HCV RNA replicon has been established stably to overcome the limitation (Lohmann, V., F. Korner, J-O Koch, U. Herian, L. Theilmann, R. Bartenschlager, 1999, Replication of subgenomic hepatitis c virus RNAs in a hepatoma cell line. Science 285:110-113). The HCV RNA replicon is divided into two categories; 1) full length replicon containing whole HCV gene and 2) subgenomic replicon in which structural proteins are excluded. The HCV RNA replicon is bicistronic replicon containing HCV 5 end, HCV IRES, neomycin resistant gene (neomycin transferase gene), and EMCV (encephalomyocarditis virus) IRES. HCV nonstructural proteins are composed of sequences comprising NS3-NS5B and HCV 3' end (untranslational region). HCV replicons against each genotype of HCV are developed (identified), which help different case studies.

JFH-1 virus (Japanese Fulminant Hepatitis-1 Virus) was first isolated from 32 year-old Japanese male patient with acute liver malfunction in 2005 (Wakita et al.), and is 2a genotype of Hepatitis C virus. JFH-1 infected with Huh7.5.1 liver cell line can replicate infectious virus and thus it is applicable to estimate anti-HCV agent or to study HCV pathology.

Ginseng has been used as a tonic agent for life extension in oriental medicine (Yun, 2001). Ginseng has been reported to have activities of treating disorders related to central nerves system, cardiovascular disease, endocrinal disorder, immune disease and aging disorder, and has been using as thermogenics, biological controller and the like (Liu and Xiao, 1992; Seong et al., 1995; Kitts et al., 2000; Bae et al., 2006). Recently, it is reported that Ginseng shows anticancer activities for appendix adenocarcinoma, B16 malignant melanoma (Mochizuki et al., 1995; Iishi et al., 1997; Liu et al., 2004), and inhibits prostate cancer cell growth (Keum et al., 2003; Kim et al., 2004) and ovary cancer (Nakata et al., 1998).

It is known that one of major active ingredients is ginsenoside (Attele et al., 1999; Yuan and Wu, 2002). Ginseng is generally comprised of 30 more ginsenosides, and each of them shows various pharmacological activities (Tanaka et al., 1986; Banthorpe, 1994; Yue et al., 2007). It has been reported that ginsenoside Rg3 especially exhibits both strong anticancer activity and anti-metastasis activity (Mochizuki et al., 1995; Shinkai et al., 1996; Iishi et al., 1997; Liu et al., 2000; Pan et al., 2002; Chen et al., 2003, 2008; Keum et al., 2003; Korean Patent Publication No. 10-2011-0106006; Kim et al., 2004; Panwar et al., 2005; Wang et al., 2006, 2007; Zhang et al., 2006; Xu et al., 2007; Kwon et al., 2008; Lu et al., 2008; Luo et al., 2008).

Red ginseng (Ginseng Radix Rubro), is obtained via a steam processed treatment at 98~100° C. for 2~3 hours. During the steam treatment processes, the amount of ginsenosides increases significantly (Kim et al., 2000; Wang et al., 2006), and such processed ginseng (red ginseng) with enhanced ginsenosides shows superior pharmacological activities than a raw ginseng (Jung and Jin, 1996; Wang et al., 2006).

On the other hand, as a description of ginsenosides, Korean Patent Publication No. 10-2012-0031588 discloses pharmaceutical composition for enhancing bone formation comprising 20(S)-ginsenoside Rh2 as an active ingredient, Korean Patent Publication No. 10-2011-0122580 discloses pharmaceutical composition for treating autoimmune disease comprising ginsenoside I as an active ingredient, Korean Patent Publication No. 10-2011-0117760 discloses pharmaceutical composition for anti-stress comprising red ginseng extract which has enhanced ginsenoside Rg3 content as an active ingredient, and Korean Patent Publication No. 10-2011-0057895 discloses skin composition for external application for increasing formation of hyaluronic acids comprising ginsenoside Re and ginsenoside compound K. However, it has not been known that ginsenoside Rg3 may be used as an agent for preventing or treating Hepatitis C.

As a final result of hard working studies to find a safe and no side effect hepatitis C preventing and treatment product, these inventors have found that ginsenoside Rg3 isolated from red ginseng has excellent activities of antiviral and apoptosis against Hepatitis C virus cells, reducing TNF-α and thioredoxin levels significantly, and increasing phospho-NFκB. It also shows the same effect of PegInterferone alpha-2b(PegIFN a-2b, Hepatitis C therapeutics), and has no cytotoxicity. Therefore, the inventors completed this invention by confirming the ginsenoside Rg3 may be used safely as a pharmaceutical composition or a health food composition for preventing or treating Hepatitis C.

SUMMARY OF THE INVENTION

The purpose of this invention is to provide a pharmaceutical compound and a health food compound containing ginsenoside Rg3 or its pharmaceutically acceptable salt as an active ingredient for preventing and treating Hepatitis C infection Another purpose of this invention is to provide a treatment method for Hepatitis C infection including the steps of administering ginsenoside Rg3 or its pharmaceutically acceptable salts to a patent in need of treatment.

The third purpose of this invention is to provide a treatment method for Hepatitis C infection which includes the steps of administering 0.1 to 100 mg of ginsenoside Rg3 as an active ingredient to a patient in need of treatment.

To comply with the above mentioned purposes, this invention provides a pharmaceutical compound for Hepatitis C prevention and treatment by administering ginsenoside Rg3 or its pharmaceutically acceptable salt as an active ingredient.

This invention also provides a health food compound for Hepatitis C prevention and its improvement by administering ginsenoside Rg3 or its pharmaceutically acceptable salt as an active ingredient.

This invention also provides a treatment method for Hepatitis C infection which includes the steps of administering ginsenoside Rg3 to a patient in need of treatment.

This invention also provides a method for hepatitis C treatment including the processes of administering 0.1 to 100 mg of ginsenoside Rg3 as an active ingredient to a patient in need of treatment.

The ginsenoside Rg3 shows the excellent antiviral activities and apoptosis actions in the Huh 7.5.1 cells infected with Hepatitis C virus in a dose-dependent manner, reducing sTNF-α and thioredoxin levels significantly, and increasing phospho-NFκB. It also shows the same effect as PegInterferone alpha-2b(PegIFN a-2b, Hepatitis C therapeutics), and has no cytotoxicity. Therefore, the ginsenoside Rg3 can be used safely as a pharmaceutical compound with no side effect for preventing or treating Hepatitis C infection.

BRIEF DESCRIPTION OF THE DRAWINGS

The above and other objects, features and other advantages of the present invention will be understood more clearly given the following detailed descriptions in conjunction with accompanying drawings, in which.

DESCRIPTION OF THE PREFERRED EMBODIMENTS

Features and advantages of this invention will be understood more clearly given the following detailed descriptions on the preferred embodiments by reference accompanying drawings. It is first noted that terms and words used herein should be construed with meanings or concepts corresponding to the technical spirit of this invention, which is based on the principle of only the inventors can appropriately define the terms and words following to concepts of their own invention. Also, it should be understood that detailed descriptions of well-known functions and structures related to this invention were dropped out not to unnecessarily obscure the important point of this invention.

Hereafter, the detailed descriptions of this invention follow.

This invention provides a pharmaceutical compound containing ginsenoside Rg3 or its pharmaceutically acceptable salts as an active ingredient for preventing or treating Hepatitis C infection. Above stated ginsenoside Rg3 is desirably depicted in the chemical formula below [Formula 1] but not limited thereto.

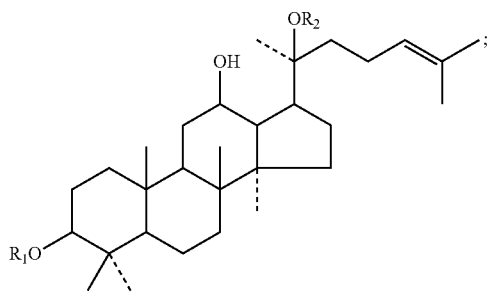

[Formula 1]

$R_1$ is Glc2-Glc; and
$R_2$ is H.

Above ginsenoside Rg3 isolated from ginseng, raw ginseng, white ginseng and red ginseng is suitable and one isolated from red ginseng is more suitable but not limited thereto.

The compound of [Formula 1] of this invention can be used in the form of ginsenoside Rg3 and its pharmaceutically acceptable alkali added salts will be more useful. The description of "pharmaceutically acceptable salts" means that they are organic and inorganic material added salts based on the formula 1 alkaline compound and the concentration of the salts should be relatively non-toxic and harmless while the side effects of the salts do not diminish the effectiveness of the formula 1 compound.

It includes alkaline metal salts (sodium salt, potassium salt etc.) and alkaline earth metal salts (calcium salt, magnesium salt) and the like. For example, the salts of aluminum, arginine, benzathine, calcium, choline, diethylamine, diolamine, glycine, lysine, magnesium, meglumine, olamine, potassium, sodium, tromethamine, zinc and the like can be included.

Also, ginsenoside Rg3 represented by formula 1 in this invention includes not only pharmaceutically acceptable salts but also the salts prepared by traditional methods, isomers, hydrates and solvates. Following to this invention, salt additions can be manufactured by the traditional methods. For example, it can be manufactured by the way of dissolving the formula 1 compound in water-miscible organic solvents, such as acetone, methanol, ethanol, acetonitrile and the like, and adding an excess quantity of base into it and then precipitation or crystallization followed. And then the salt additions can be obtained when the mixture is dried out by removing the solvent, or by further processing of suction filtration of the mixture.

Figure 1:
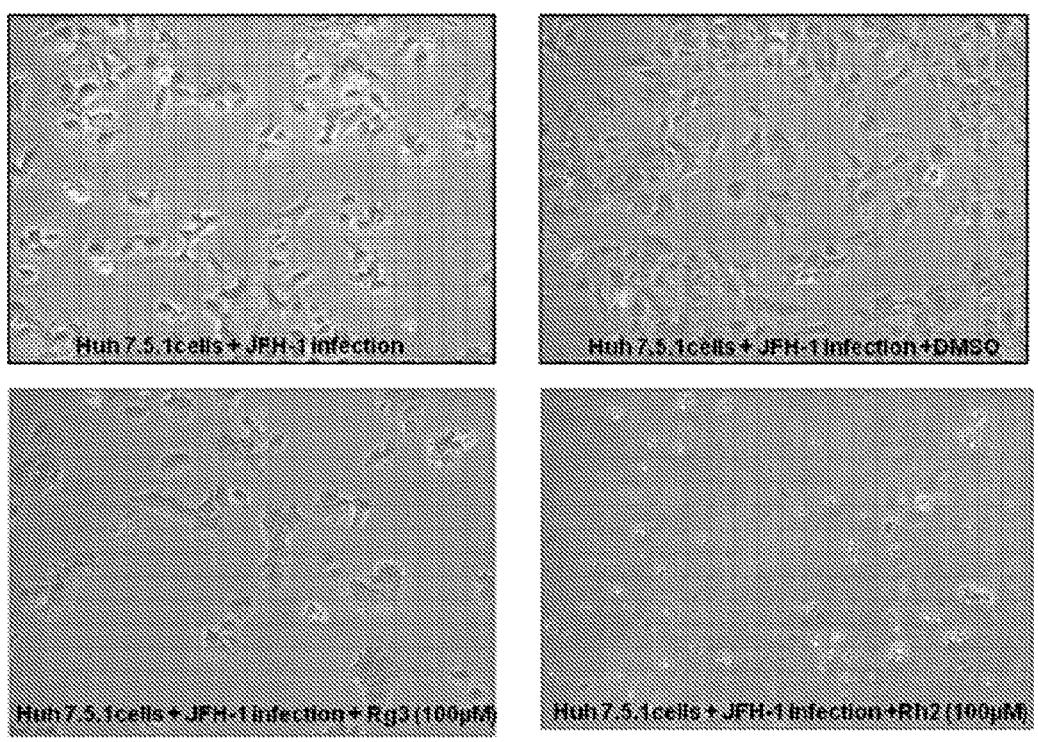
FIG. 1 shows the effects of test samples of Huh 7.5.1 cells treated with 7 kinds of ginsenosides (24 hours after the treatment, microscopic photograph).
Figure 2:
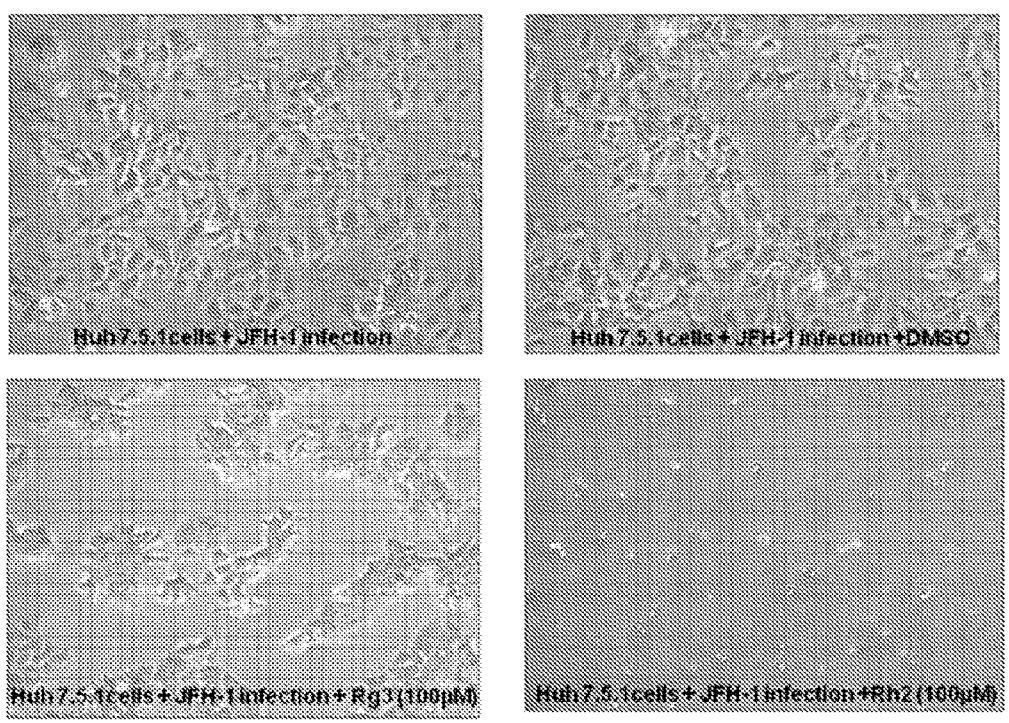
FIG. 2 shows the effects of test samples of Huh 7.5.1 cells treated with 7 kinds of ginsenosides (72 hours after the treatment, microscopic photograph).

Described the specific examples in this invention, we, inventors used Huh 7.5.1 cell line which was well known as a cell line infected easily with hepatitis C virus (JFH-1). To use for the experiments the Huh 7.5.1 cell was infected with JFH-1 virus after the cell was incubated and seeded. The Huh 7.5.1 cell was treated with 100 μM each of seven ginsenosides (Ro, Re, Rg1, Rg2, Rg3, Rh1, Rh2) and investigated the shape of each cell treated after 24 and 72 hours. The ginsenoside Rg3 treated group showed cell-fusion while the control group and JFH-1 virus infected group did not show any cell-fusion (FIG. 1 and FIG. 2)

Figure 3:
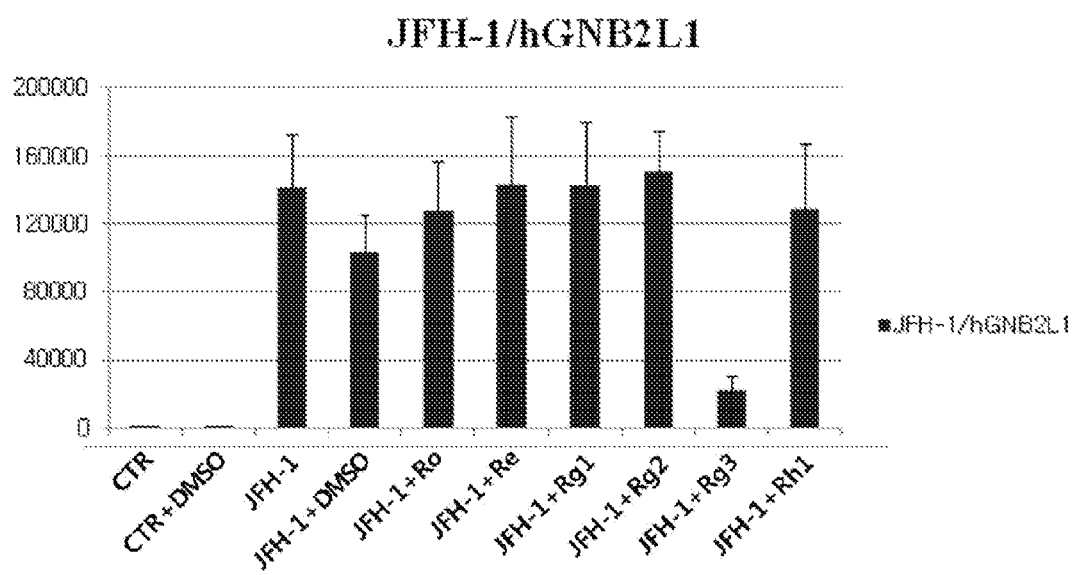
FIG. 3 shows the real time PCR results of JFH-1 mRNA after Huh 7.5.1 cells treated with 7 kinds of ginsenosides.

To identify the inhibitory activity of ginsenoside Rg3 on hepatitis C virus, the Huh 7.5.1 cell was treated with 100 μM each of the seven ginsenosides, and 72 hours after the cell was treated, the real time PCR to JFH-1 mRNA was conducted. The result showed that the level of JFH-1 mRNA remarkably decreased in the cell group of 100 μM of ginsenoside Rg3 treated (FIG. 3).

Figure 4:
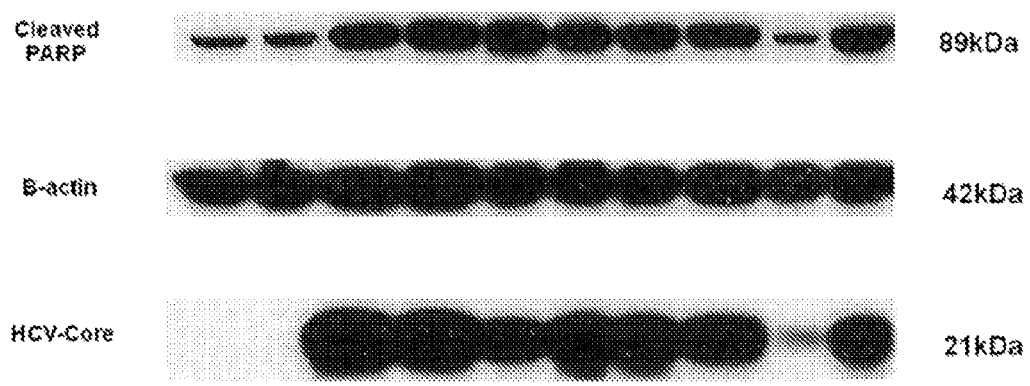
FIG. 4 shows the results of western blot analysis for HCV CORE and cleaved PARP in apoptosis after treating 7 kinds of ginsenosides.

To identify the virus inhibition activity of ginsenoside Rg3, the Huh 7.5.1 cell was treated with 100 μM each of the seven ginsenosides and 72 hours after that, a western blotting analysis onto HCV CORE and cleaved PARP in apoptosis was carried out. The HCV CORE was remarkably decreased and cleaved PARP was also decreased in the treated cell group (FIG. 4).

Figure 5:
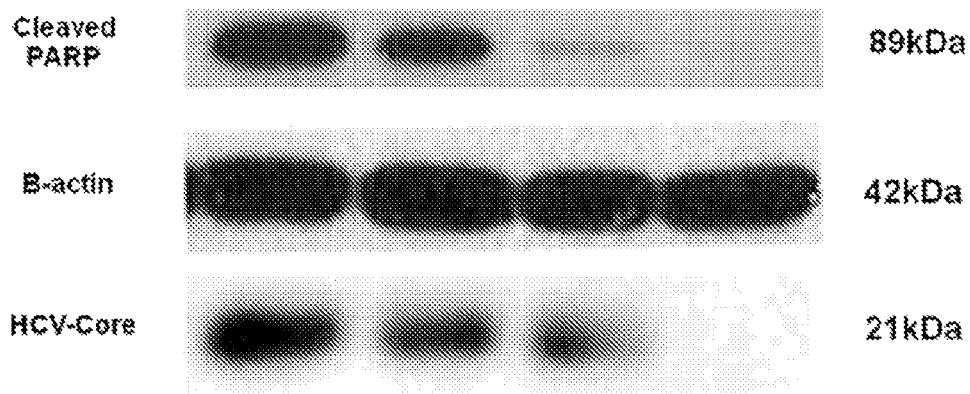
FIG. 5 shows the results of western blotting for HCV CORE and cleaved PARP in concentrations of 10 μM, 25 μM, 50 μM and 100 μM of Rg3.

To examine the antiviral effect of ginsenoside Rg3 (in the dose-dependent manner), a western blotting was conducted in 10 μM, 25 μM, 50 μM and 100 μM of ginsenoside Rg3 onto HCV CORE and cleaved PARP, and the result was both the levels of virus and apoptosis were inhibited in a dose-dependent manner in the cell group of ginsenoside Rg3 treated (FIG. 5).

Figure 6:
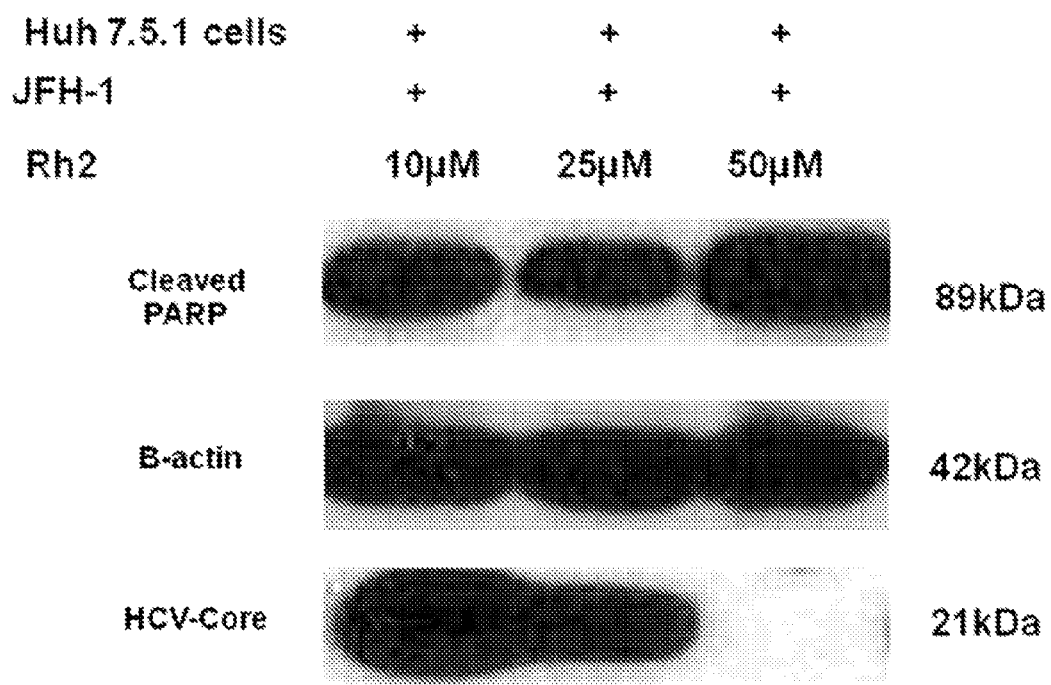
FIG. 6 shows the results of western blotting for HCV CORE and cleaved PARP in concentrations of 10 μM, 25 μM and 50 μM of Rh2.

As a result of an examination of antiviral effect of ginsenoside Rh2, the virus was decreased in the concentration of less than 50 μM of ginsenoside Rh2 in a dose-dependent manner, however no apoptosis relationship showed in a dose-independent manner (FIG. 6).

Figure 7:
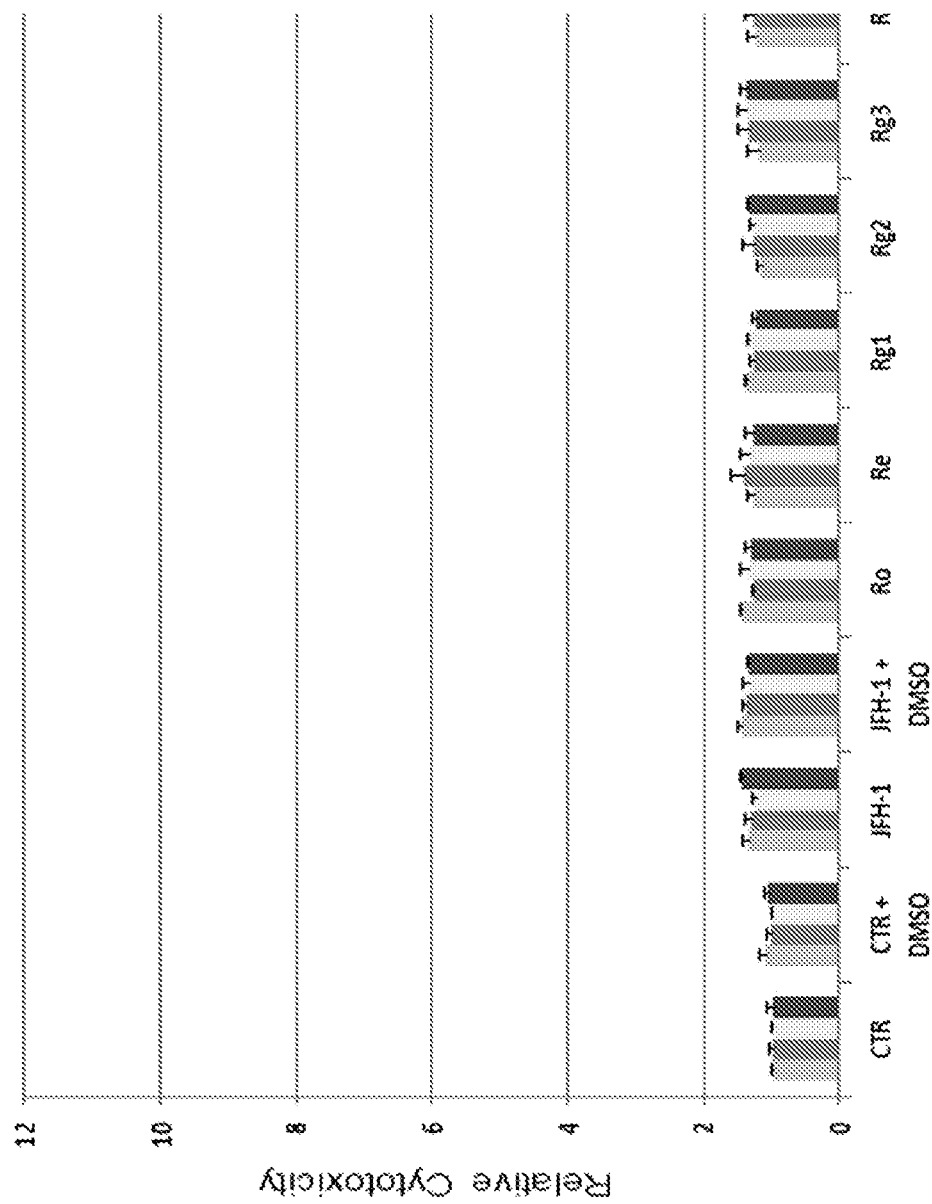
FIG. 7 shows the results of MTT assay to identify cytotoxicity of ginsenosides.

To examine the cytotoxicity of ginsenoside, an MTT assay was conducted. The JFH-1 virus infected Huh 7.5.1. cells were treated with ginsenosides and identified that no cytotoxicity appeared (FIG. 7).

Figure 8:
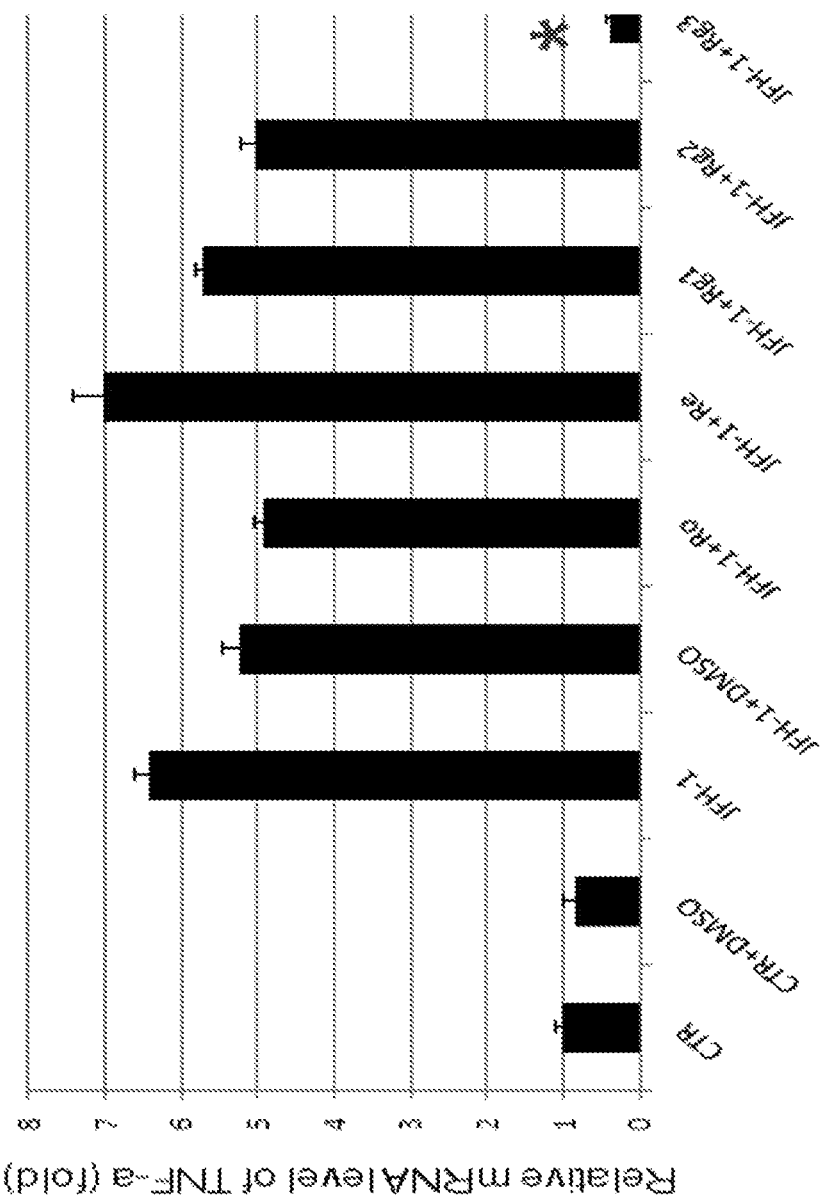
FIG. 8 shows the results of real time PCR for TNF-α to identify inhibition mechanism of apoptosis of ginsenoside Rg3.

To identify the mechanism of cytotoxicity action in ginsenoside Rg3, virus infected Huh 7.5.1 cell was treated with ginsenoside Rg3, and a real time PCR was conducted to check the level of TNF-alpha. The level of TNF-alpha was increased in the virus-infected cells, however the level of TNF-alpha was remarkably decreased in the cell group of ginsenoside Rg3 treated (FIG. 8).

Figure 9:
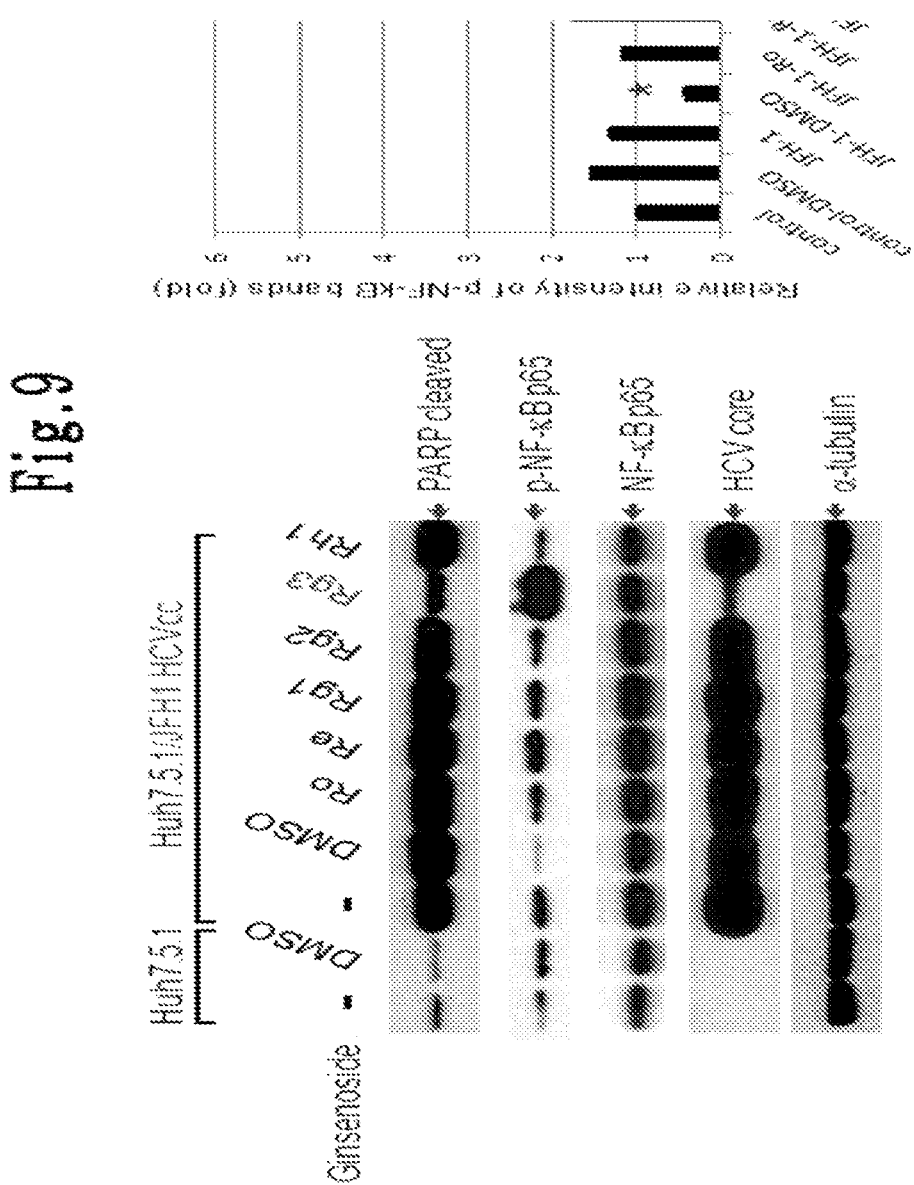
FIG. 9 shows the results of western blotting for NFκB to identify inhibition mechanism of apoptosis of ginsenoside Rg3.

To examine a virus inhibition mechanism of ginsenoside in liver cancer cell line, a western blotting was conducted onto the transcription factors of NFκB and phospho-NFκB. The level of phospho-NFκB (active form of NFκB) was decreased in virus-infected group and apoptosis was increased whereas the level of phospho-NFκB was remarkably decreased and apoptosis significantly decreased in the cell group of ginsenoside Rg3 treated (FIG. 9).

Figure 10:
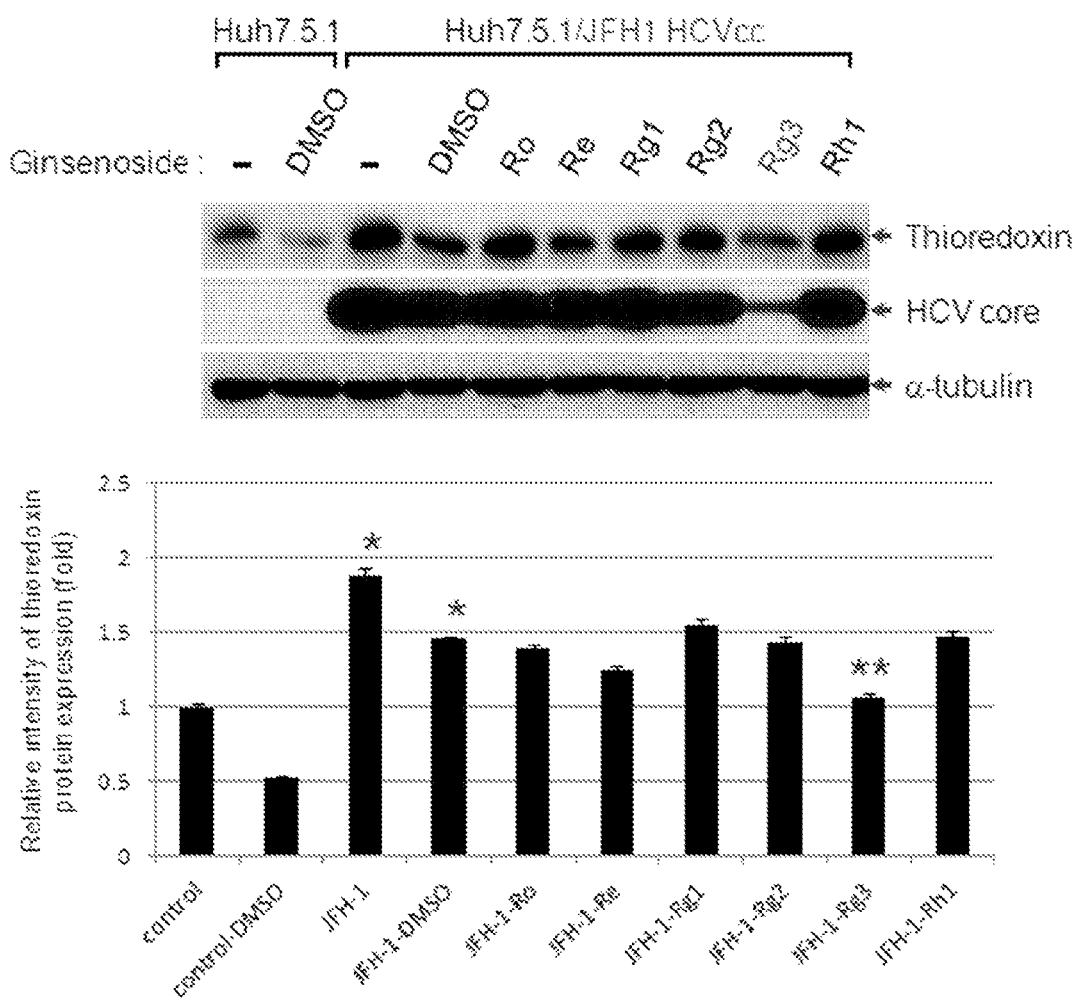
FIG. 10 shows the effects of antioxidant enzymes of ginsenoside Rg3.

To identify an anti-oxidant enzyme effect of ginsenoside Rg3, a western blotting analysis against thioredoxin, one of anti-oxidant enzymes caused by hepatitis c inflammation, was carried out after treating the cells with the ginsenosides. The level of thioredoxin was increased in Hepatitis c virus infected cells while the level was decreased in the ginsenoside Rg3 treated cells (FIG. 10).

Figure 11:
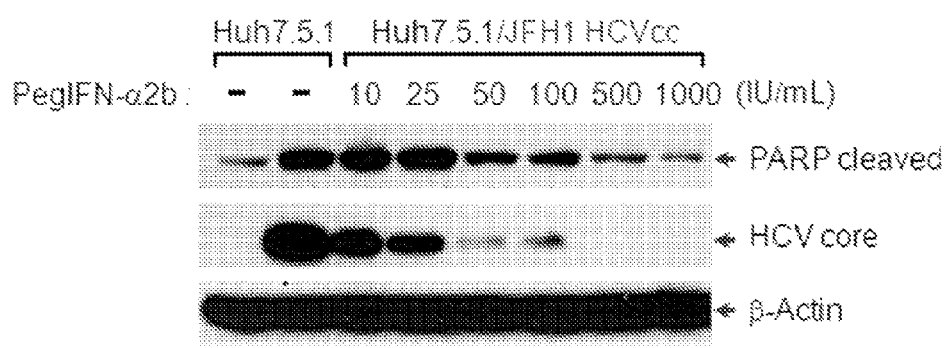
FIG. 11 shows the inhibition effect for virus and apoptosis by PegIFN a-2b.

Hepatitis C virus (JFH-1) infected Huh 7.5.1 cells were treated with PegIFN alpha-2b (which is currently used for Hepatitis C patients) and analyzed the effect against HCV CORE and cleaved PARP by conducting a western blotting assay. The virus level and apoptosis were decreased in Hepatitis C virus-infected cell group in a dose inversely-dependent manner when the interferon was treated with different doses (FIG. 11).

Therefore, the ginsenoside Rg3 and/or its pharmaceutically acceptable salts of the presented invention may be used as an active ingredient for preventing and treating hepatitis C since the ginsenoside Rg3 or its pharmaceutically acceptable salts have excellent both antiviral and apoptosis activities against Hepatitis C virus cells (Huh 7.5.1) in a dose-dependent manner, activities of reducing the levels of TNF-α and thioredoxin significantly, and increasing the level of phospho-NFκB, and it shows the same effect of PegInterferone alpha-2b(PegIFN a-2b, Hepatitis C therapeutics), and has no cytotoxicity.

In case of the composition of the presented invention is used as a medical/pharmaceutical product, the above stated ginsenoside Rg3 and its pharmaceutically acceptable salts may be administrated in various oral or non-oral formulations, but not limited to, when clinically administered. As for oral administration, it may be used in the formulations of tablets, pills, capsules (hard/soft), solutions, suspensions, emulsions, syrups, granules, elixirs and the like, and such formulations may contain its active ingredient, diluents (e.g., lactose, dextrose, sucrose, mannitol, sorbitol, cellulose and/or glycine), carriers (e.g., silica, talc, stearic acid, stearic magnesium or stearic calcium and/or polyethylene glycol). The tablets may contain binders like magnesium, aluminium, silicate, starch paste, gelatin, methylcellulose, sodium carboxymethylcellulose and/or polyvinylpyrrolidine, and occasionally contain dissolving agents like sodium salts of starch, agar, or arginic acid, and boiling mixtures and/or absorbents, colorants, flavouring agents, and sweeting agents.

The above stated ginsenoside Rg3 and its pharmaceutically acceptable salts may be administrated non-orally. When non-orally administered, it may be used in a way of subcutaneous injection, intravenous injection, intramuscular injection, or intrathoracic injection. When it is formulated for non-oral administrations, it may be formulated in ampules or vials by mixing the above stated ginsenoside Rg3 and its pharmaceutically acceptable salts with stabilizer or buffer solution and water to make solutions or suspensions. The above stated composition may be sterilized and/or to be sterilized, and contain antiseptic agents, stabilizers, wettable agents or emulsifiers, salts and/or buffers for controlling osmotic pressure, and therapeutically useful agents. The composition may be formulated by traditional methods such as mixing, granulating, or coating.

The administration dosage of the composition to human may vary depends on a patient's age, weight, gender, formulation of the product, health condition, and the disease severity degree. In case standardized to 70 Kg man, general dosage may be 0.1 mg to 1,000 mg/day, preferably 1~500 mg/day, and the daily dosage may be administered once or divided over a few times per day at a decision made by a doctor or a pharmacist.

The presented invention also provides health food composition for preventing or improving Hepatitis C with ginsenoside Rg3 or its pharmaceutically acceptable salts.

The above stated ginsenoside Rg3 of the present invention may be desirably depicted by [formula 1], but not limited thereto.

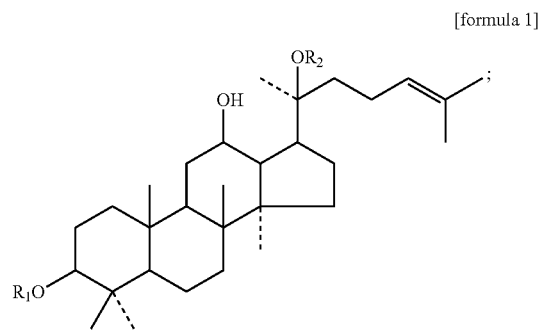

[formula 1]

$R_1$ is Glc2-Glc; and
$R_2$ is H.

The ginsenoside Rg3 isolated from ginseng, raw ginseng, white ginseng and red ginseng is desirable and the one isolated from red ginseng is more desirable, but not limited thereto.

The ginsenoside Rg3 or its pharmaceutically acceptable salts has excellent dose-dependent antiviral activities and apoptosis actions against Hepatitis C virus cells (Huh 7.5.1), reduces levels of TNF-α and thioredoxin, and increases phospho-NFκB. It shows the same effect of PegInterferone alpha-2b(PegIFN a-2b, Hepatitis C therapeutics), and has no cytotoxicity, and thus it may be used safely as an active ingredient for health foods for preventing or improving Hepatitis C.

There are no specific limits in kind to be the above stated foods. For food examples, it includes commonly understandable health foods such as all kinds of drinks, meat, sausages, breads, biscuits, rice cakes, chocolates, candies, snacks, pizzas, noodles, gums, ice creams, milk products, soups, alcohol/non-alcohol drinks, and vitamin complex, but not limited thereto.

The ginsenoside Rg3 or its pharmaceutically acceptable salts of this invention may be added to food directly, or used with another food or food ingredients following to the ways of commonly used, but not limited thereto. The amount of the active ingredient may be determined following to the purpose of use (prevention or improvement). Generally, for the health food use, the ginsenoside Rg3 or its pharmaceutically acceptable salts may be added into the food at the rate of 0.01-15 wt %, and the health drink composition may be made at the rate of 0.02-5 g/100 mL drinks, or desirably added at the rate of 0.3 g-1 g/100 mL drinks. However, in case of long-term intakes for improving health and sanitation, or regulating health conditions, the above stated adding dosage rates may be lowered while higher rates of the active ingredients may be used since the active ingredients has no safety problems. The health food drink composition may require only to have the directed rates of the ginsenoside Rg3 or its pharmaceutically acceptable salts in the drinks but no limitations in adding various flavoring agents or natural carbohydrates as an additive in common drinks, but not limited thereto. To take examples for the above stated natural carbohydrates, they may be monosaccharides, (e.g., glucose, fructose, and etc.), disaccharides (e.g., maltose, sucrose and etc.), polysaccharides such as commonly used sugars, (e.g., dextrin, cyclodextrin, and etc.), and alcohol sugars (e.g., xylitol, sorbitol, erythrytol, and etc.). Beyond the above stated articles, as a flavoring agent, natural flavoring agents such as taumatin, stevia extract (e.g., levaudioside A, glycyrrhyzine etc.), and synthetic flavoring agents such as saccharine, aspartame, and etc.) may be beneficially added. The natural carbohydrates may be added at the rate of 1-20 g/100 mL invented composition, or desirably 5-12 g/100 mL invented composition.

The ginsenoside Rg3 or its pharmaceutically acceptable salts of the presented invention may contain various nutritional supplements, vitamins, minerals (electrolytes), synthetic flavoring agents and natural flavoring agents, colorants and enhancers (cheese, chocolate etc.), pectic acid and its salt, arginic acid and its salt, organic acids, protective colloidal thickeners, pH adjusters, stabilizers, antiseptic agents, glycerin, alcohols, and carbonates for carbonated beverages. The ginsenoside Rg3 or its pharmaceutically acceptable salts of the presented invention may contain fruit flesh for manufacturing natural fruit juice, fruit juice beverages, and vegetable juice. These ingredients may be used independently or in conjunction with other ingredient(s). While the rate of the additives is not critical, it may be generally used at the rate of 0-20 additives/100 ginsenoside Rg3 or its pharmaceutically acceptable salts part by weight.

Hereafter, the presented invention procedures will be described in more detail with reference annotations to following experimental examples and preoperational examples.

However, the following experimental examples and preoperational examples are for providing invention concepts and illustration only. The actual scope of the presented invention should not be limited thereto in any manner.

Implementation Example 1

Acquisition of Ginsenosides

Ginsenosides used in the presented invention were purchased from Ambo Research Institute (Daejeon, Republic of Korea).

Implementation Example 2

Hepatoma Cell Line (Huh 7.5.1) Culturing and Division

Experiments in the present invention utilized Huh 7.5.1 cell, Hepatoma cell line, since the Huh 7.5.1 cell was well known as the cell line to be most easily infected with Hepatitis C virus (JFH-1) through current experimental models of Hepatitis C virus <2-1> Huh 7.5.1 Cell Culturing After taking out Huh 7.5.1 cell stock vial which was kept in LN2 (nitrogen) tank, the Huh 7.5.1 cell stock vial warmed up in 37° C. water bath for 1½ minutes to 2 minutes. Then, the thawed Huh 7.5.1 cells were transferred to a cornical tube and mixed with 10 mL complete media (CM). The mixture centrifuged for 5 minutes at 1000 RPM, and the supernatant of the mixture collected. And then, after mixing the pellet in the cornical tube with 1 mL complete media, the mixture was transferred to a cell culture dish and 10 ml CM was added. And then, the cell culture dish was shaken in cross patterns to spread the Huh 7.5.1 cells out evenly. Then, the Huh 7.5.1 cells were cultured in a 5% $CO_2$ incubator at 37° C.

<2-2> Huh 7.5.1 Cell Division

After taking out the cell culture dish from the incubator (37° C., 5% CO2) culture media were collected. The collected culture media were washed with 1×PBS (phosphate buffered saline) once and collected again. Then, 3 mL trypsin-EDTA per 100×20 mm cell culture dish each was added. The dish was shaken to sufficiently cover the surface. And then, the dish was laid in a 5% $CO_2$ incubator at 37° C. for 1½ minutes. After that, the Huh 7.5.1 cells were collected from the dish and put into a cornical tube, and added 10 ml CM. And the mixture was centrifuged for 5 minutes at 1000 RPM, and the supernatant of the mixture collected. And then, pellet in the cornical tube was mixed with 1 mL CM and the mixture was transferred to a 100×20 mm cell culture dish and 10 ml CM was added to the dish. The cell culture dish was shaken in cross patterns to spread the Huh 7.5.1 cells evenly out. Then, the Huh 7.5.1 cells were cultured in a 5% $CO_2$ incubator at 37° C.

Implementation Example 3

Virus Infection and Ginsenosides Treatment

About 200,000 Huh 7.5.1 cells were added to a 60×15 mm cell culture dish and every 100 μM of seven ginsenosides (Ro, Re, Rg1, Rg2, Rg3, Rh1, Rh2) per 60×15 mm cell culture dish each was treated. Since it was necessary for ginsenosides in powder formulation to make solutions for the experiments, 50 mM basic concentration solutions for the seven ginsenosides each were prepared and the basic solutions were refrigerated at 4° C. until they were needed.

Specific design of the experiment follows.

Non-treatment group (Control), Non-treatment group and DMSO 10 μl treatment group (Control+DMSO 10 μl), JFH-1 virus treatment group (Only JFH-1), JFH-1 virus and DMSO 10 μl treatments group (JFH-1+DMSO 10 μl), JFH-1 virus and Ro 100 uM treatments group (JFH-1+Ro 100 uM), JFH-1 virus and Re 100 uM treatments group (JFH-1+Re 100 uM), JFH-1 virus and Rg1 100 uM treatments group (JFH-1+Rg1 100 uM), JFH-1 virus and Rg2 100 uM treatments group (JFH-1+Rg2 100 uM), JFH-1 virus and Rg3 100 uM treatments group (JFH-1+Rg3 100 uM), JFH-1 virus and Rh1 100 uM treatments group (JFH-1+Rh1 100 uM), JFH-1 virus and Rh2 100 uM treatments group (JFH-1+Rh2 100 uM), JFH-1 virus and Rg1 100 uM treatments group (JFH-1+Rg1 100 uM).

The experiment was carried out as follow. First, 200,000 Huh 7.5.1 cells were placed in a 60×15 mm cell culture dish. Next day, Japanese Fulminant Hepatitis-1 virus (JFH-1) stock vial which was stored in −70° C. refrigerator was taken out and thawed out in a container filled with ice-water. The culture medium was collected from the cultured 60×15 mm cell culture dish, washed with 1×PBS and collected, again. 1.5 ml of JFH-1 virus solution per 60×15 mm cell culture dish each was added. The dish was shaken to cover the surface sufficiently. The dish was laid in a 5% $CO_2$ incubator at 37° C. for 6 hours and after that, the supernatant was draw out. 1×PBS was spread on the cell surface as slow as possible and after one time washing, cells were collected. 5 ml of cell culture media was added to control and JFH-1 treatments groups. At the last step of virus-infection, 5 ml CM and each 10 μM of ginsenosides which was set to 50 mM concentration were added to the cell culture media. After that, the cell culture media was laid in a 5% $CO_2$ incubator at 37° C. After 72 hours, the following steps were carried out.

Implementation Example 4

Identification of Virus Suppression Effect with Ginsenosides Treatment on Hepatoma Cell Line After the virus-infected Huh 7.5.1 cells were treated with ginsenosides, virus suppression effect was identified.

<4-1> Microscopic Identification of Virus Suppression Effect.

As described in the above Example 3, each 100 μM of seven ginsenosides (Ro, Re, Rg1, Rg2, Rg3, Rh1, Rh2) was treated to Huh 7.5.1 cells. After 24 hours and 72 hours, the shapes of Huh 7.5.1 cells were observed using a phase contrast microscope (ECLIPSE TE300, Nicon) of 400× magnifications.

The results were shown in FIGS. 1 and 2. At 24 hours after the Huh 7.5.1 cells were treated with ginsenosides, it was observed that ginsen oside Rg3 treatment group (JFH-1+Rg3 100 uM) fuses cells unlike both the control group and the JFH-1 virus treatment group. No cell were remained due to the apoptosis of all cells in the Rh2 treatment group (JFH-1+Rh2 100 uM). The rest groups showed similar cells' shapes with the control group and the JFH-1 virus treatment group (FIG. 1).

Meanwhile, at 72 hours after the Huh 7.5.1 cells treated with ginsenosides, it was observed that ginsenoside Rg3 treatment group (JFH-1+Rg3 100 uM) fuses cells unlike both the control group and the JFH-1 virus treatment group and the fusion is more than after 24 hours. No cell were remained due to the apoptosis of all cells in the Rh2 treatment group (JFH-1+Rh2 100 uM). The rest of the groups showed similar cells' shapes with the control group and the JFH-1 virus treatment group (FIG. 2).

<4-2> Real-Time PCR Identification of Virus Suppression Effect.

As described in the above Example 3, the Huh 7.5.1 cells were treated with each 100 µM of seven ginsenosides (Ro, Re, Rg1, Rg2, Rg3, Rh1, Rh2). After 72 hours, a real-time PCR against JFH-1 mRNA was carried out. In this case hgNB2L1 was a house-keeping gene.

Specific real-time PCR carried out was as follow. First, 50,000 Huh 7.5.1 cells were cultured in a 24 well. After that, total RNA was extracted from the cells treated by the above described method by using Rneasy mini kit (QIAGEN) and quantified by using Nanodrop 1000 (Thermo Scientific). Then, cDNA was constructed by RT-PCR (Reverse Transcription-PCR) using i cycler (BIO-RAD). In addition, a real-time PCR was carried out by using StepOne Plus (ABI) wherein used primers were as follows.

```
Human JFH-1(Applied Biosystems, Branchburg, New
Jersey):
Forward primer:
                                      (Sequence No.: 1)
5'-TCTGCGGAACCGGTGAGTA-3';
and (Sequence No.: 2)
Reverse primer:
5'-TCAGGCAGTACCACAAGGC-3'.

Human GNB2L1 (Macrogen) (House keeping gene):
Forward primer:
                                      (Sequence No.: 3)
5'-GACCATCATCATGTGGAAACTGA-3';
and (Sequence No.: 4)
Reverse primer:
5'-CCGTTGTGAGATCCCAGAGG-3'.
```

As shown in FIG. 3, it was identified that JFH-1 mRNA was remarkably decreased in the cells of ginsenoside Rg3 100 µM treatment group (JFH-1+Rg3 100 uM).

<4-3> Western Blotting Identification of Virus Suppression Effect

<4-3-1> Identification of Virus Suppression Effect by Types of Ginsenosides

As described in the above Example 3, the Huh 7.5.1 cells were treated with each 100 µM of seven ginsenosides (Ro, Re, Rg1, Rg2, Rg3, Rh1, Rh2). After 72 hours, a western blotting analysis was carried out for analyzing virus suppression effect against HCV CORE and cleaved PARP.

Specific western blotting analysis carried out was as follow. First, the above described samples were prepared, mixed with a sample buffer in tubes and heated at 100° C. for 10 minutes. The tubes were cooled on ice and centrifuged. The electrophoresis was carried out with the above samples and molecular weight markers, and then they were transferred to a PVDF membrane (hydrophobic). After blocking with 5% skin milk for an hour, each primary antibody was added. After staying overnight at 4° C., washings three times for every 10 minutes were conducted, and the blocking was carried out with 5% skin milk for an hour at the room temperature. After that, each secondary antibody was added, and the reaction for an hour and washing three times for every 10 minutes were conducted. Then, the membrane was stained by 1:1 mix with detection reagents A (Luminol Enhancer solution) and B (Peroxide solution) and developed with X ray film.

The result was shown in FIG. 4. The HCV CORE was remarkably decreased in the cells of ginsenoside Rg3 100 µM treatment group (JFH-1+Rg3 100 uM), and cleaved PARP was also decreased. Therefore, it was identified that ginsenoside Rg3 has remarkable virus suppression effect and can be used safely for the virus suppression in the cells regarding to the apoptosis of the cells is as similar as that of the cells not infected by Hepatitis C virus (FIG. 4).

<4-3-2> Identification of Dose-Dependent Anti-Virus Effect of Ginsenoside Rg3

To examine the dose-dependent anti-virus effect of ginsenoside Rg3, western blotting analysis against cleaved PARP and HCV CORE were carried out with the samples of ginsenosides Rg3 treatment concentration at 10 µM, 25 µM, 50 µM and 100 µM each.

The result was shown in FIG. 5. It was identified that the virus suppression effect and apoptosis of the cells by ginsenoside Rg3 showed in a dose-dependent manner (FIG. 5).

<4-3-3> Identification of Dose-Dependent Anti-Virus Effect of Ginsenoside Rh2

To examine the dose-dependent anti-virus effect of ginsenoside Rh2, western blotting analysis against cleaved PARP and HCV CORE were carried out with the samples of ginsenosides Rh2 treatment concentration at 10 µM, 25 µM and 50 µM each. The experiment under the treatment of ginsenoside Rh2 100 µM was not carried out since all cells became extinct under the treatment of ginsenoside Rh2 100 µM concentration.

The result was shown in FIG. 6. It was identified that the virus suppression effect and the apoptosis of the cells by ginsenoside Rh2 showed in a dose-dependent manner at the ginsenoside Rh2 concentration up to 50 µM (FIG. 6).

Implementation Example 5

Cytotoxicity Test of Ginsenosides on Liver Cancer Cell Line

MTT assay was conducted to identify cytotoxicity of ginsenosides.

Specifically, the cells (Huh7.5.1) were seeded at the rate of 1×10$^4$ cells (in 100 µL)/well in 96 well plates, and incubated in 5% $CO_2$ incubator for less than 24 hours. And after the samples were washed with 1×PBS once and treated with the rate of 50 ul JFH-1 virus/well, and replaced in the 5%, $CO_2$ incubator for six hours. After taking out the cell samples from the incubator, the samples were washed with 1×PBS once and replaced in the culturing media comprising 10, 25, 50 and 100 µL concentration of the above stated seven (7) ginsenosides in Example 3, respectively. After the cells were incubated in 5% $CO_2$ incubator for 72 hours, 20 µl of assay reagent, EZ Cytox, was seeded into each well with the care of no bubble producing. And then, the treated cells were incubated in 5% $CO_2$ incubator for 2.5 hours, followed by examining absorbance at 420 nm with Microplate Reader (Molecular Devices, Minn.). DMSO was the solvent used when treating with ginsenoside, and both the control group and the cells infected with JFH-1 group were also treated with the solvent DMSO.

JFH-1 virus infected Huh 7.5.1 cell treated with ginsenoside showed as minimal cytotoxicity as the one of control group ($1^{st}$ lane), control and DMSO treated cells ($2^{nd}$ lane), JFH-1 virus infected cells ($3^{rd}$ lane) and JFH-1 and DMSO treated cells ($4^{th}$ lane) (FIG. 7). However, when the cells were treated with 100 µM of ginsenoside Rh2 (last lane), the cytotoxic effect was shown predominantly. Therefore, it was confirmed that ginsenosides treated groups other than the group of high concentration treated with ginsenoside Rh2 produce no cytotoxicity.

Implementation Example 6

Apoptosis Inhibition Test of Ginsenoside Rg3

To identify a mechanism of apoptosis action, virus-infected Huh 7.5.1 cells were treated with ginsenoside Rg3 and conducted real-time PCR (Taqman Real-time Quantitative RT-PCR Assay for HCV RNA Detection) to estimate TNF-α level.

Description of specific real-time PCR conducted follows:
First, a total number of 50,000 Huh 7.5.1 cells were incubated in 24 well and a total RNA was extracted from the above stated treated cells using Rneasy mini kit (QIAGEN Corp.). And then, the total RNA was quantified by Nanodrop 1000 (Thermo Scientific Corp.), and manufactured cDNA by conducting RT PCR (Reverse Transcription-PCR) using i cycler, (BIO-RAD Co.). After the synthesized cDNAs were reacted with TaqMan GX Master Mix (Applied Biosystems, Branchburg, N.J.), TNF-α, B-actin mRNAs were quantified by 96 well real-time PCR (StepOne Plus Sequence detector system, Applied Biosystems). Verified primer/probe set was purchased to conduct the TaqMan Gene Expression assay in this experiment (Gene: TNF-α (TNF-alpha) # Hs01113624_g1, Gene Symbol: ACTB # Hs99999903_m1).

As the results, the level of TNF-α increased in virus-infected cell group, and remarkably decreased in the group treated with ginsenoside Rg3 (FIG. 8).

Implementation Example 7

Identification of Ginsenoside Rg3 Effect Against Anti-Apoptotic Factor

Conducted western blotting onto NFκB and phospho-NFκB which are transcription factors of virus suppression mechanism of ginsenosides to a hepatoma cell line.

Specifically, it is known that when cells are infected with hepatitis C viruses, TNF-α in the cells increases and, apoptosis actions in the cells increases due to an anti-apoptotic factor, NFkB decreases. Additionally, identification of phosphor-NFκB among NFκB (total) is important to know activation level of NFκB.

Herein, western blotting analysis onto NFkB and phospho-NFκB, transcription factors, was carried out to identify the TNF-α mediated apoptotic signaling pathway. The TNF-α is induced by Hepatitis C. The analysis was conducted 72 hours after the samples of Huh 7.5.1 cells treated with each 100 µM of seven ginsenosides (Ro, Re, Rg1, Rg2, Rg3, Rh1, Rh2) as above stated in Example 3.

Specifically, the western blotting analysis was carried out as follow. First, the above described samples were prepared, mixed with a sample buffer in tubes and heated at 100° C. for 10 minutes. The tubes were cooled on ice and centrifuged. The electrophoresis was carried out with the prepared samples and molecular weight markers were put in. And then, they were transferred to a PVDF membrane (hydrophobic). After blocking with 5% skin milk for an hour, primary antibodies of NFκB and phospho-NFκB were added. After staying overnight at 4° C., washing three times for every 10 minutes were conducted and the blocking with 5% skin milk for an hour at the room temperature was carried out. After that, each secondary antibody was added, and the reaction for one hour and the following three times washings for every 10 minutes were carried out. Then, the membrane was stained by 1:1 mix with detection reagents A (Luminol Enhancer solution) and B (Peroxide solution) and developed with X ray film.

As the results shown in FIG. 9. the phospho-NFκB which is the activated type of NFκB (an anti-apoptotic factor) was decreased when infected with Hepatitis C virus, and so the apoptosis of cells was increased. However the phospho-NFκB was increased in cells when the samples were treated with ginsenoside Rg3, and so the apoptosis of cells was remarkably decreased (FIG. 9).

Implementation Example 8

Effects of Ginsenoside Rg3 on Antioxidant Enzymes

To examine the ginsenoside Rg3 effect onto anti-oxidant enzymes, western blotting analysis against thioredoxin, an anti-oxidant enzyme induced by Hepatitis C, was carried out. the analysis was conducted 72 hours after the samples of Huh 7.5.1 cells treated with each 100 µM of seven ginsenosides (Ro, Re, Rg1, Rg2, Rg3, Rh1, Rh2) as described above in the Example 3.

Specifically, western blotting analysis was carried out as follow. First, the above described samples were prepared, mixed with a sample buffer in tubes, and heated at 100° C. for 10 minutes. The tubes were cooled on ice and centrifuged. The electrophoresis was carried out with the prepared samples and molecular weight markers were put in. And then, they were transferred to a PVDF membrane (hydrophobic). After blocking with 5% skin milk for an hour, primary antibodies of thioredoxin was added. After staying overnight at 4° C., washing three times for every 10 minutes, blocking with 5% skin milk for an hour at the room temperature was carried out. After that, each secondary antibody was added and waited one hour for its reaction and washing three times for every 10 minutes were carried out. Then, the membrane was stained by 1:1 mixture of detection reagents A (Luminol Enhancer solution) and B (Peroxide solution) and developed with X ray film.

As the results shown in FIG. 10, thioredoxin was increased in the cells infected with Hepatitis while it was decreased in the cells treated with ginsenoside Rg3 (FIG. 10).

Implementation Example 9

Interferon Effect Against Virus Inhibition and Apoptosis

To analyze the effect onto HCV CORE and cleaved PARP, western blotting analysis was carried out with the samples of Huh 7.5.1 cells infected with Hepatitis C virus, JFH-1 treated each with 10, 25, 50, 100, 500 and 1000 IU/mL of PegIFN alpha-2b which is currently used to cure Hepatitis C patients.

Specifically, western blotting analysis was carried out as follow. After the above stated samples prepared, they were mixed with sample buffer in tubes, heated at 100° C. for 10 minutes, and then cooled on ice and centrifuged. The electrophoresis was carried out with the prepared samples and molecular weight markers were put in. And then, they were transferred to a PVDF membrane (hydrophobic). After blocking with 5% skin milk for an hour, HCV CORE and primary antibody cleaved PARP were added. After staying overnight at 4° C., washing three times for every 10 minutes and blocking with 5% skin milk for an hour at the room temperature was carried out. After that, each secondary antibody was added and waited one hour for its reaction and washing three times for every 10 minutes were carried out. Then, the membrane was stained by 1:1 mixture of detection reagents A (Luminol Enhancer solution) and B (Peroxide solution) and developed with X ray film.

As the results shown in FIG. 11, the levels of both virus and apoptosis in the Hepatitis C virus infected sample group was inversely proportional by increasing the concentration of treated interferon. It confirmed that the ginsenoside Rg3 of the presented invention has as same anti-virus effect as the interferon therapeutics (FIG. 11).

Implementation Example 10

HCV NS3/4A Protease Activity

HCV Protease Assay kit (ANASPEC) was used to the following experiments. The components, description and quantity were as follows:

TABLE 1

HCV Protease Assay Kit

| Component | Description | Quantity |
|---|---|---|
| Component A | HCV NS3/4A protease substrate Ex/Em = 490 nm/520 nm upon cleavage | 120 μL |
| Component B | 5-FAM, fluorescence reference standard Ex/Em = 490 nm/520 nm upon cleavage | 100 μM, 5 μL |
| Component C | 2X Assay buffer | 10 mL |
| Component D | Stop solution | 10 mL |
| Component E | DTT | 1M, 0.5 mL |
| Component F | Pep4AK | 50 μL, 600 μM |

Other required materials were as follows:

96-well or 384-well microplate: Black, flat-bottom 96-well or 384-well plate with nonbinding surface.

Fluorescence microplate reader: Capable of detecting emission at 520 nm with excitation at 490 nm.

HCV NS3 protease: AnaSpec provides highly active recombinant HCV NS3/4A protease (Cat#61017).

Storage and Handling conditions were as follows:

Stored all kit components at −20° C.

Protected Components A and B from light

Components C and D could be stored at room temperature for convenience

<Preparation of Working Solutions>

(A) Assay Buffer:

Prepared fresh assay buffer for each experiment

TABLE 2

| Assay buffer for one 960well plate (100 assays) | |
|---|---|
| Components | Volume |
| 2X assay buffer (Component C) | 5 mL |
| 1M DTT (Component E) | 300 μL |
| Deionized water | 5 mL |
| Total volume | 10 mL |

(B) HCV NS3/4A Protease Substrate Solution:

Diluted HCV protease substrate (Component A) 1:50 in assay buffer.

For each experiment, fresh substrate solution was prepared.

TABLE 3

| HCV protease substrate solution for one 96-well plate (100 assays) | |
|---|---|
| Components | Volume |
| HCV protease substrate (50X, Component A) | 100 μL |
| Assay buffer | 4.9 mL |
| Total volume | 5 mL |

(C) HCV NS Protease Diluent:

Diluted HCV NS3 protease to an appropriate concentration in assay buffer.

(D) Activated HCV NS3 Protease.

a) Pep4AK diluent: Diluted Pep4AK (Component F) 1:100 in assay buffer.

b) Mixed an equal volume of the HCV NS3 protease diluent and Pep4AK diluent. Incubated the mixture at 23-25° C. for 15 min.

(1) 520 HCV Protease Assay

The process of sample preparation (NS3 containing cellular membrane fractions) is as follows:

The HCV replicon-containing cells (e.g. $1 \times 10^7$-$10^8$ Huh7 cells) grew to 90% confluence. The cells were washed with 1× phosphate-buffered saline once, and then the cells were detached by scraping. The cell pellets were harvested by centrifuging at 900×g for 10 min at 4° C. The cell pellets were resuspended with 1 mL of hypotonic buffer (10 mM Tris-HCl, pH 7.8, 10 mM NaCl), and then the cell pellets were incubated on ice for 15-20 min. The cell pellets were disrupted with 50 strokes of a tight fitting pestle in a Dounce homogenizer. The homogenate was centrifuged at 900×g for 5 min at 4° C. to remove the nuclei, which was in the pellet. The supernatant was collected, which contained membrane fractions, and centrifuged it at 15,000×g for 20 min at 4° C. to pellet the cellular membrane. The supernatant was discarded and the pellet was resuspended in 100-500 μL of storage buffer (hypotonic buffer plus 15% glycerol), and then continued to protocol for HCV NS3 protease assay. Typically, membrane from $1 \times 10^6$ cells was used for one assay. (Membrane fractions can be stored at −80° C. for later use, good for up to 3 months.)

(2) Measuring HCV NS3/4A Protease Activity in Biological Samples (A) Set Up Enzymatic Reaction.

50 μL/well (96-well plate) or 20 μL/well (384-well plate) of HCV NS3/4A protease containing biological sample was added. At the same time, the following control wells were set up, as deemed necessary:

Positive control contained HCV NS/4A protease standard.

Negative control contained biological sample without HCV NS/4A protease.

Substrate control contained deionized water.

Also, the total volume of all the controls was brought up to 50 μL (96-well plate) or 20 μL (384-well plate).

(B) Initiate the Enzymatic Reaction.

1) 50 μL (96-well plate) or 20 μL (384-well plate) of substrated solution was added. The reagents were mixed completely by shaking the plate gently for 30-60 sec.

2) fluorescence signal was measured:

For kinetics reading: Immediately started measuring fluorescence intensity at Ex/Em=490 nm/520 nm continuously and recorded data every 5 min for 30 to 60 min.

For end-point reading: Incubated the reaction at room temperature for 30 to 60 minutes. Kept the plate from direct light. Optional: Added 50 μL/well (96-well plate) or 20 μL/well (384-well plate) of stop solution (Component D). Then measured fluorescence intensity at Ex/Em=490 nm/520 nm.

<Inhibition of NS3/4 Protease Activity>

Figure 12:
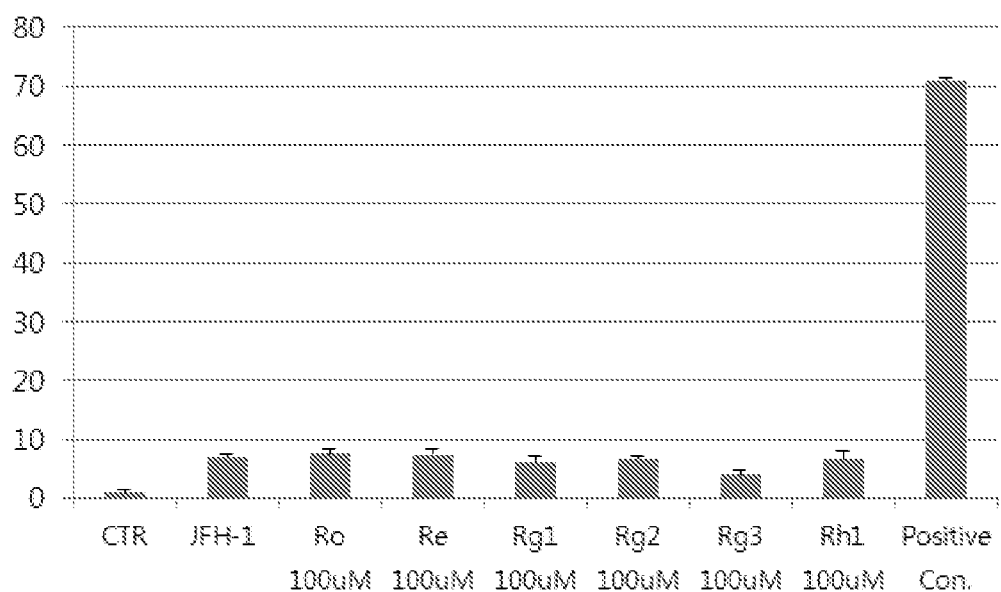
FIG. 12 shows the inhibition effect of Rg3 for NS3/4 protease.
Figure 12:
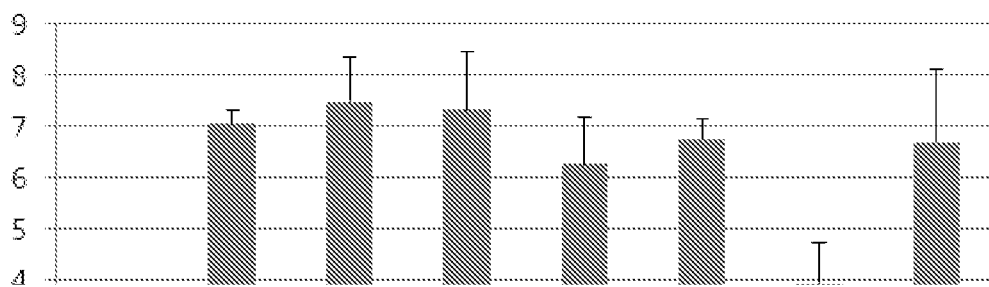
Figure 13:
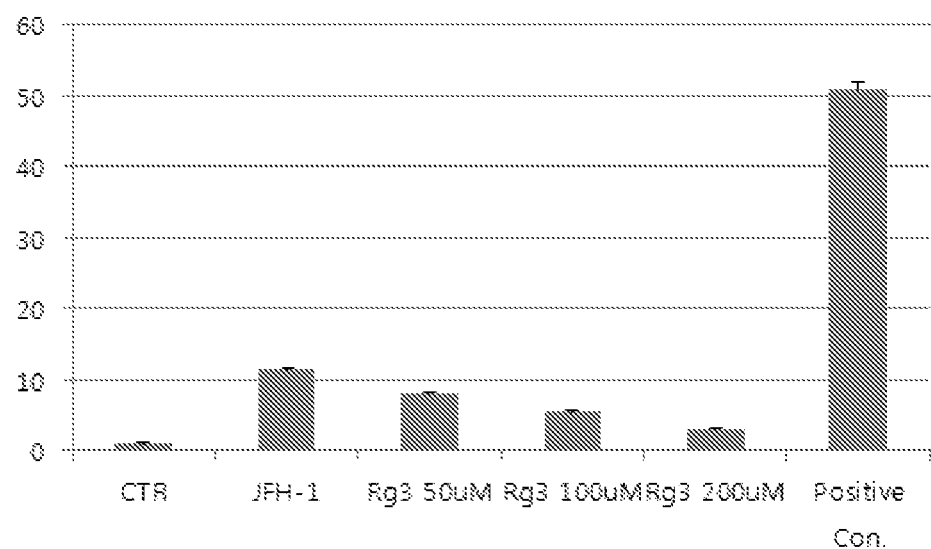
FIG. 13 shows the inhibition effect of Rg3 for NS3/4 protease in the dose-dependent manner.
Figure 13:
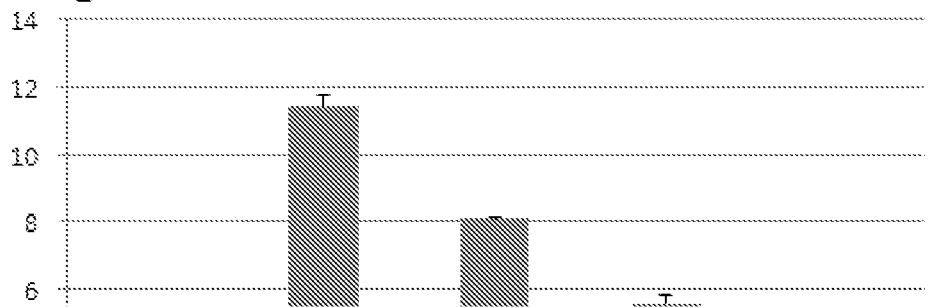

As a result, NS3/4 protease activity was inhibited by the treatment of Rg3 (FIG. 12) and in a dose-dependent manner (FIG. 13). Thus, it is thought that Rg3 was one of the effective NS3/4 protease inhibitors.

Manufacturing Example 1

Preparation of Pharmaceutical Formulations

<1-1> Preparation of Tablets

The 200 g ginsenoside Rg3 complying with the <Implementation Example 1> of the presented invention was mixed with 175.9 g of lactose, 180 g of potato starch and colloidal silicic acid. After adding 10% gelatin solution to the mixture, it was sifted through a sieve (14 mesh-sieve). After the mixture dried out, added potato starch 160 g, talc 50 g and magnesium stearate 5 g. And then, the mixture was formulated into tablets.

<1-2> Preparation of Injections

The 1 g ginsenoside Rg3 complying with the <Implementation Example 1> of the presented invention was dissolved with 0.6 g of NaCl and 0.1 g of ascorbic acid, and marked up to 100 mL. the prepared liquid was bottled in and sterilized by heating up at 20° C. for 30 minutes.

Manufacturing Example 2

Preparation of Food

<2-1> Preparation of Flour Food Products

The ginsenoside Rg3 complying with the <Implementation Example 1> of the presented invention was added to flour at the rate of 0.1-5.0 weight %. Using this mixture bread, cake, cookies, crackers, or noodles were made for improving human health.

<2-2> Preparation of Milk Products

The ginsenoside Rg3 complying with the <Implementation Example 1> of the presented invention was added to milk at the rate of 0.1-1.0 weight %. Using the mixed milk, butter, ice cream, or other milk products were made.

<2-3> Preparation of Drinks

The 0.5 g ginsenoside Rg3 complying with the <Implementation Example 1> of the presented invention was added to 1000 ml tomato juice or carrot juice to make vegetable juices for improving human health.

What is claimed is:

1. A method for treatment of hepatitis C, comprising administering ginsenoside Rg3 or pharmaceutically acceptable salt thereof to a patient in need of treatment.

2. A method for treatment of hepatitis C, comprising administering the composition which includes 0.1 to 100 mg of ginsenoside Rg3 as an effective ingredient to a patient in need of treatment.

3. The method according to claim 2, characterized in that the composition is in a form selected from pills, hard capsules, soft capsules, liquids, suspensions, emulsifiers, syrups and granules.

* * * * *

SEQUENCE LISTING

```
<160> NUMBER OF SEQ ID NOS: 4

<210> SEQ ID NO 1
<211> LENGTH: 19
<212> TYPE: DNA
<213> ORGANISM: Artificial Sequence
<220> FEATURE:
<223> OTHER INFORMATION: Human JFH-1 Forward primer for pcr

<400> SEQUENCE: 1
tctgcggaac cggtgagta                                                  19

<210> SEQ ID NO 2
<211> LENGTH: 19
<212> TYPE: DNA
<213> ORGANISM: Artificial Sequence
<220> FEATURE:
<223> OTHER INFORMATION: Human JFH-1 Reverse primer for pcr

<400> SEQUENCE: 2
tcaggcagta ccacaaggc                                                  19

<210> SEQ ID NO 3
<211> LENGTH: 23
<212> TYPE: DNA
<213> ORGANISM: Artificial Sequence
```

```
<220> FEATURE:
<223> OTHER INFORMATION: Human GNB2L1 Forward primer for pcr

<400> SEQUENCE: 3
gaccatcatc atgtggaaac tga                                              23

<210> SEQ ID NO 4
<211> LENGTH: 20
<212> TYPE: DNA
<213> ORGANISM: Artificial Sequence
<220> FEATURE:
<223> OTHER INFORMATION: Human GNB2L1 Reverse primer for pcr

<400> SEQUENCE: 4
ccgttgtgag atcccagagg                                                  20
```